United States Patent
Kleyman et al.

(10) Patent No.: US 8,968,187 B2
(45) Date of Patent: Mar. 3, 2015

(54) ARTICULATING LAPAROSCOPIC SURGICAL ACCESS INSTRUMENT

(75) Inventors: Gennady Kleyman, Brooklyn, NY (US); Eric Taylor, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 142 days.

(21) Appl. No.: 13/467,406

(22) Filed: May 9, 2012

(65) Prior Publication Data

US 2012/0296169 A1     Nov. 22, 2012

Related U.S. Application Data

(60) Provisional application No. 61/487,933, filed on May 19, 2011.

(51) Int. Cl.
*A61B 1/32*     (2006.01)
*A61B 1/00*     (2006.01)
*A61B 1/313*     (2006.01)

(52) U.S. Cl.
CPC ............ *A61B 1/00149* (2013.01); *A61B 1/3132* (2013.01)
USPC .......................................... 600/204; 600/215

(58) Field of Classification Search
CPC ............... A61B 17/34; A61B 17/3417; A61B 17/3421; A61B 17/3431; A61B 17/3443
USPC .............. 600/201–246; 74/422, 89.11–89.12, 74/89.16–89.19
See application file for complete search history.

(56) References Cited

U.S. PATENT DOCUMENTS

| | | | | |
|---|---|---|---|---|
| 1,607,662 | A | * | 11/1926 | Boynton ........................ 175/228 |
| 1,750,953 | A | * | 3/1930 | Boynton ........................ 175/267 |
| 2,209,054 | A | * | 7/1940 | Doud et al. ...................... 454/63 |
| 3,610,058 | A | * | 10/1971 | Loyd et al. .................... 74/89.17 |
| 4,898,577 | A | | 2/1990 | Badger et al. |
| 4,997,419 | A | | 3/1991 | Lakatos et al. |
| 5,318,589 | A | * | 6/1994 | Lichtman ....................... 606/205 |
| 5,441,483 | A | | 8/1995 | Avitall |
| 5,498,231 | A | * | 3/1996 | Franicevic .................... 600/190 |
| 5,507,725 | A | | 4/1996 | Savage et al. |
| 5,549,637 | A | * | 8/1996 | Crainich ........................ 606/207 |
| 5,743,880 | A | | 4/1998 | Hlavka |
| 5,836,958 | A | * | 11/1998 | Ralph ............................ 606/160 |
| 6,309,403 | B1 | * | 10/2001 | Minor et al. ................... 606/205 |
| 6,770,026 | B2 | * | 8/2004 | Kan et al. ....................... 600/114 |
| 6,837,642 | B1 | * | 1/2005 | Lin ............................. 403/109.1 |
| 6,858,005 | B2 | | 2/2005 | Ohline et al. |
| 7,111,769 | B2 | | 9/2006 | Wales et al. |

(Continued)

*Primary Examiner* — Eduardo C Robert
*Assistant Examiner* — Jacqueline Johanas

(57) ABSTRACT

A surgical instrument includes proximal and distal shaft components, an articulation assembly, and an outer sleeve. The shaft components are pivotably coupled to one another. The distal shaft component is articulatable relative to the proximal shaft component between a substantially aligned configuration and an articulated configuration. The articulation assembly includes a rack and a pinion gear engaged with one another. The rack and the pinion gear cooperate to permit incremental articulation of the distal shaft component relative to the proximal shaft component between the substantially aligned and articulated configurations. The outer sleeve is disposed about the proximal shaft component and is manipulatable relative to the proximal shaft component between a first position and a second position for articulating the distal shaft component between the substantially aligned configuration and the articulated configuration.

7 Claims, 5 Drawing Sheets

(56) References Cited

U.S. PATENT DOCUMENTS

| | | | |
|---|---|---|---|
| 7,250,027 B2 | 7/2007 | Barry | |
| 7,540,872 B2 | 6/2009 | Schechter et al. | |
| 7,637,903 B2 | 12/2009 | Lentz et al. | |
| 7,682,319 B2 | 3/2010 | Martin et al. | |
| 7,708,182 B2 | 5/2010 | Viola | |
| 7,749,228 B2 * | 7/2010 | Lieberman | 606/84 |
| 7,811,277 B2 | 10/2010 | Boulais | |
| 8,006,365 B2 * | 8/2011 | Levin et al. | 29/432 |
| 8,052,710 B2 * | 11/2011 | Kambin et al. | 606/192 |
| 8,105,233 B2 * | 1/2012 | Abou El Kheir | 600/166 |
| 8,479,969 B2 * | 7/2013 | Shelton, IV | 227/180.1 |
| 8,584,921 B2 * | 11/2013 | Scirica | 227/179.1 |
| 8,708,213 B2 * | 4/2014 | Shelton et al. | 227/180.1 |
| 2002/0169362 A1 * | 11/2002 | Kan et al. | 600/170 |
| 2004/0138701 A1 * | 7/2004 | Haluck | 606/205 |
| 2005/0006434 A1 * | 1/2005 | Wales et al. | 227/180.1 |
| 2005/0014995 A1 | 1/2005 | Amundson et al. | |
| 2007/0049966 A1 | 3/2007 | Bonadio et al. | |
| 2007/0078302 A1 | 4/2007 | Ortiz et al. | |
| 2007/0208312 A1 | 9/2007 | Norton et al. | |
| 2008/0009747 A1 | 1/2008 | Saadat et al. | |
| 2008/0027279 A1 * | 1/2008 | Abou El Kheir | 600/111 |
| 2008/0097391 A1 | 4/2008 | Feinberg et al. | |
| 2008/0147109 A1 * | 6/2008 | Kambin et al. | 606/190 |
| 2008/0188869 A1 | 8/2008 | Weitzner et al. | |
| 2008/0281293 A1 | 11/2008 | Peh et al. | |
| 2009/0157076 A1 | 6/2009 | Athas et al. | |
| 2009/0188965 A1 * | 7/2009 | Levin et al. | 227/179.1 |
| 2009/0192495 A1 | 7/2009 | Ostrovsky et al. | |
| 2010/0121147 A1 | 5/2010 | Oskin et al. | |
| 2010/0280533 A1 * | 11/2010 | Martinez et al. | 606/158 |
| 2011/0054479 A1 * | 3/2011 | Aram et al. | 606/87 |
| 2011/0152878 A1 * | 6/2011 | Trusty et al. | 606/130 |
| 2012/0253132 A1 * | 10/2012 | Davis | 600/201 |
| 2012/0289946 A1 * | 11/2012 | Steger | 606/1 |
| 2013/0178712 A1 * | 7/2013 | Malkowski et al. | 600/208 |
| 2013/0178713 A1 * | 7/2013 | Kleyman et al. | 600/219 |
| 2013/0178837 A1 * | 7/2013 | Malkowski | 606/1 |

* cited by examiner

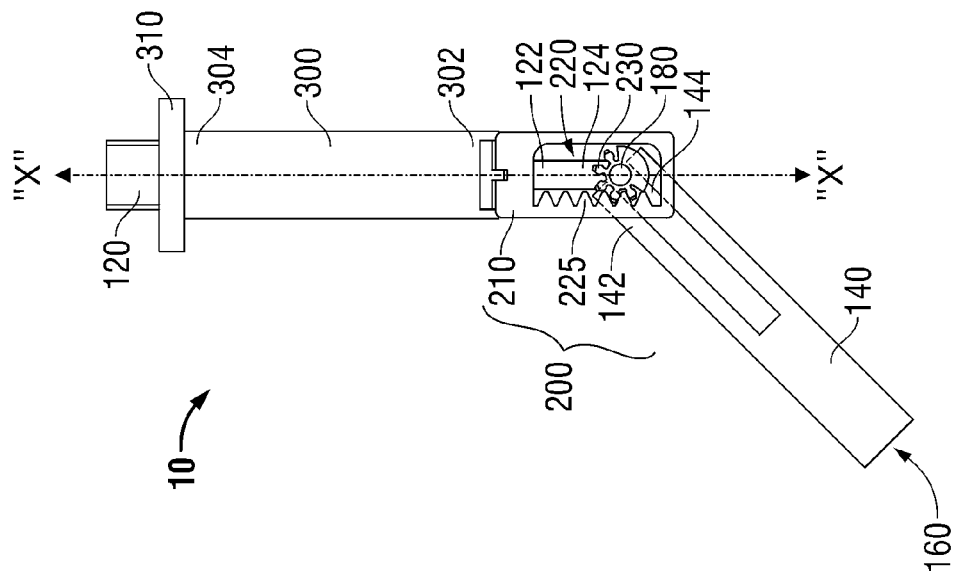
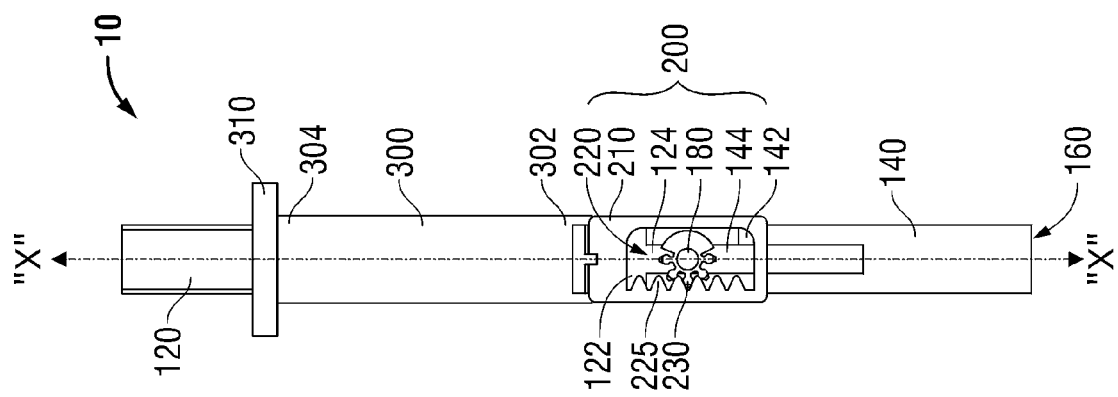

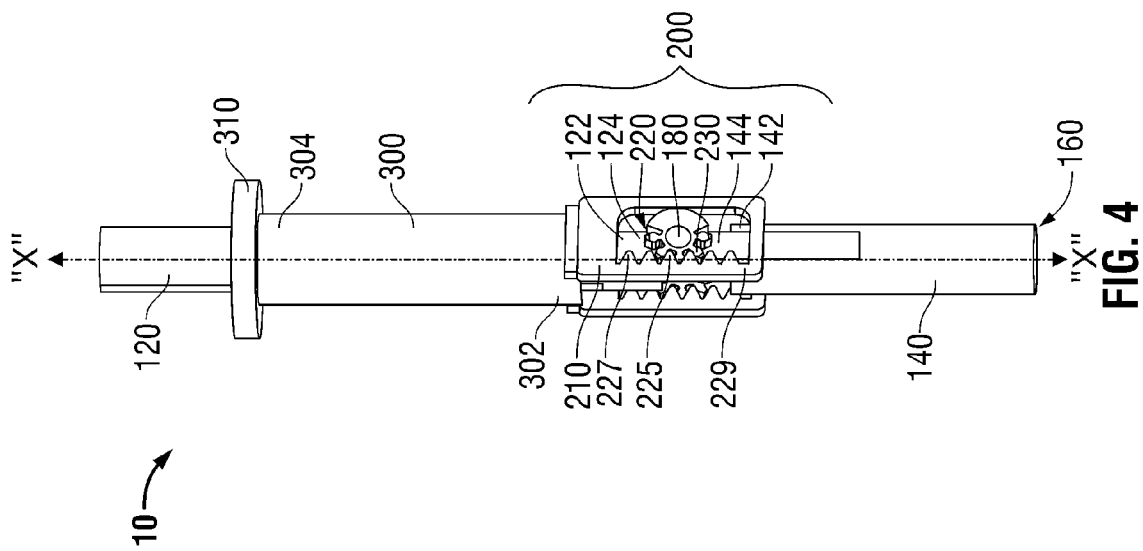
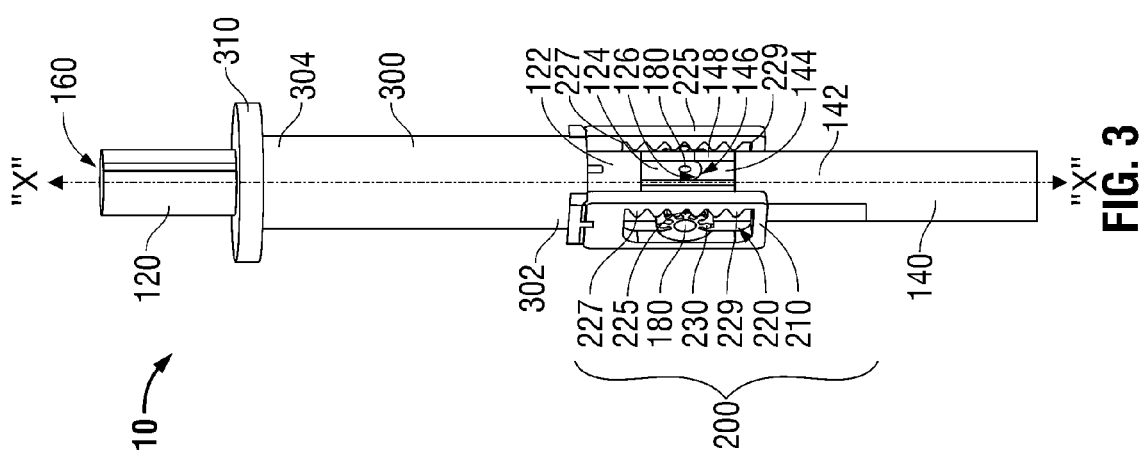

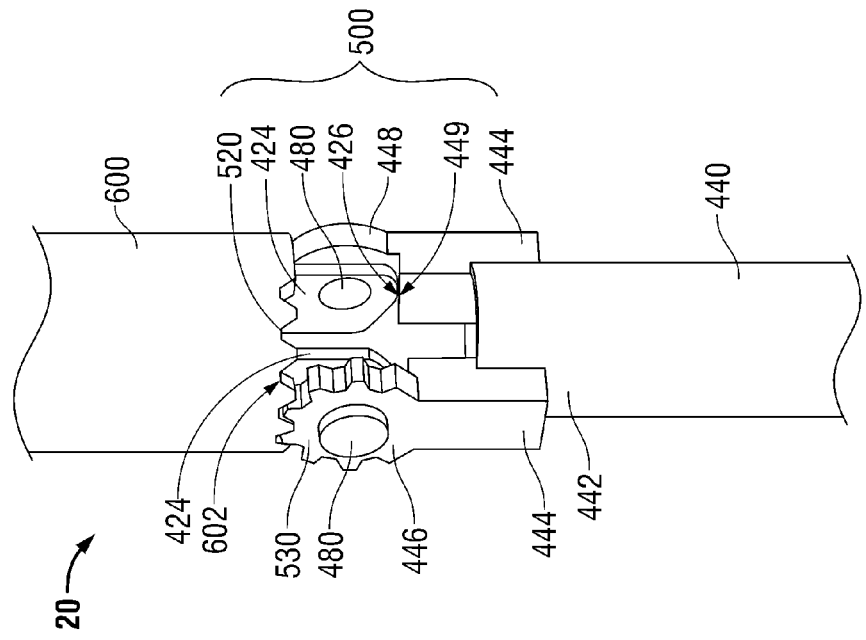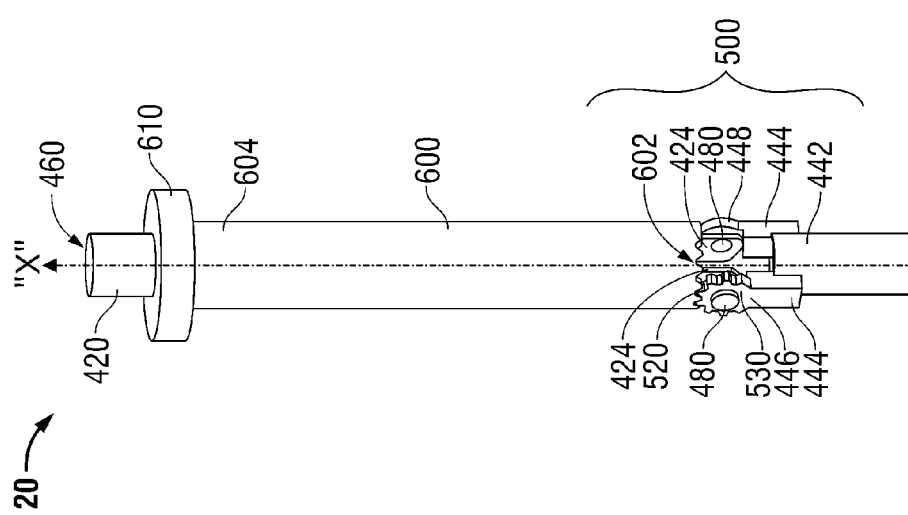

ARTICULATING LAPAROSCOPIC SURGICAL ACCESS INSTRUMENT

CROSS-REFERENCE TO RELATED APPLICATIONS

This application claims the benefit of and priority to U.S. Provisional Patent Application No. 61/487,933, filed May 19, 2011, the entire disclosure of which is incorporated by reference herein.

BACKGROUND

1. Technical Field

The present disclosure relates to a surgical access device, and more particularly, to an articulating surgical access instrument for use in laparoscopic surgical procedures.

2. Background of Related Art

In laparoscopic and endoscopic surgical procedures, a small incision or puncture is made in a patient's body, e.g., in the abdomen, to provide an entry point for a surgical access device which is inserted into the incision and facilitates the insertion of instruments used in performing surgical procedures within an internal surgical site. Laparoscopic surgical procedures are advantageous in that, as compared to traditional open surgical procedures, both trauma to the patient and recovery time are reduced due to the relatively small incisions formed through the patient's body. However, since these access incisions are small, only the elongated, small diametered instrumentation may be used to access the internal body cavities and organs.

During such procedures, surgical objects such as surgical access devices, e.g., trocar and cannula assemblies, are inserted into the patient's body through the incision in tissue. In general, prior to the introduction of the surgical object into the patient's body, insufflation gases are used to enlarge the area surrounding the target surgical site to create a larger, more accessible work area.

The surgeon is then able to perform the procedure within the abdominal cavity by manipulating the instruments that have been extended through the access devices. The manipulation of such instruments within the internal body is similarly limited by both spatial constraints and the need to maintain the body cavity in an insufflated state.

SUMMARY

In accordance with one embodiment of the present disclosure, a surgical instrument including a proximal shaft component, a distal shaft component, an articulation assembly, and an outer sleeve is provided. The proximal shaft component defines a longitudinal axis and is pivotably coupled to the distal shaft component such that the distal shaft component is articulatable relative to the proximal shaft component between a substantially aligned configuration, wherein the proximal and distal shaft components are disposed about the longitudinal axis, and an articulated configuration, wherein the distal shaft component is articulated off of the longitudinal axis. The articulation assembly includes a rack and a pinion gear engaged with one another and configured to permit incremental articulation of the distal shaft component relative to the proximal shaft component between the substantially aligned and articulated configurations. The outer sleeve is disposed about the proximal shaft component and is selectively manipulatable, e.g., translatable or rotatable, relative to the proximal shaft component between a first position and a second position for moving the distal shaft component between the substantially aligned configuration and the articulated configuration.

In one embodiment, the proximal and distal shaft components cooperate with one another to define a lumen extending longitudinally therethrough for receipt of surgical instrumentation therethrough.

In another embodiment, the proximal and distal shaft components each include one or more arms extending therefrom towards the other shaft component. In one embodiment, the proximal and distal shaft components each include a pair of opposed arms. The arms of the proximal and distal shaft components are pivotably coupled to one another to permit articulation of the distal shaft component between the substantially aligned configuration and the articulated configuration. Further, one or more of the arms may define a mating surface configured to facilitate articulation of the distal shaft component relative to the proximal shaft component. The mating surface may also include a stop feature configured to inhibit articulation of the distal shaft component relative to the proximal shaft component beyond a pre-determined position.

In another embodiment, the outer sleeve includes a proximal rim disposed at the proximal end thereof. The proximal rim is configured to facilitate manipulation of the outer sleeve relative to the proximal and distal shaft components.

In yet another embodiment, the outer sleeve is longitudinally translatable along the longitudinal axis and relative to the proximal shaft component between the first position and the second position for articulating the distal shaft component between the substantially aligned configuration and the articulated configuration. In such an embodiment, the articulation assembly may include one or more brackets extending from the distal end of the outer sleeve and defining the rack therein. The distal shaft component may include one or more arms extending therefrom that include the pinion gear disposed thereon. The pinion gear(s) is engaged with the rack(s) such that translation of the outer sleeve between the first and second positions articulates the distal shaft component between the substantially aligned configuration and the articulated configuration.

In still yet another embodiment, the outer sleeve is rotatable about the longitudinal axis and relative to the proximal shaft component between the first position and the second position for articulating the distal shaft component between the substantially aligned configuration and the articulated configuration. In such an embodiment, the rack may define an annular configuration disposed circumferentially about at least a portion of a distal surface of the outer sleeve. The distal shaft component may include one or more arms extending therefrom, each of which includes a pinion gear. The pinion gear(s) is engaged with the rack on the distal surface of the outer sleeve such that rotation of the outer sleeve between the first and second positions articulates the distal shaft component between the substantially aligned configuration and the articulated configuration.

BRIEF DESCRIPTION OF THE DRAWINGS

Various embodiments of the present disclosure are described hereinbelow with reference to the drawings, wherein:

FIG. 1 is a side view a surgical access instrument provided in accordance with one embodiment of the present disclosure, wherein the instrument is disposed in a substantially straight configuration;

FIG. 2 is a side view of the surgical access instrument of FIG. 1, wherein the instrument is disposed in an articulated configuration;

FIG. 3 is a top, perspective view of the surgical access instrument of FIG. 1, wherein the instrument is disposed in the substantially straight configuration;

FIG. 4 is a side, perspective view of the surgical access instrument of FIG. 1, wherein the instrument is disposed in the substantially straight configuration;

FIG. 5 is a perspective view of another embodiment of a surgical access instrument provided in accordance with the present disclosure, wherein the instrument is disposed in the substantially straight configuration;

FIG. 6 is an enlarged, perspective view of the articulation assembly of the surgical access instrument of FIG. 5;

DETAILED DESCRIPTION OF EMBODIMENTS

Figure 8:
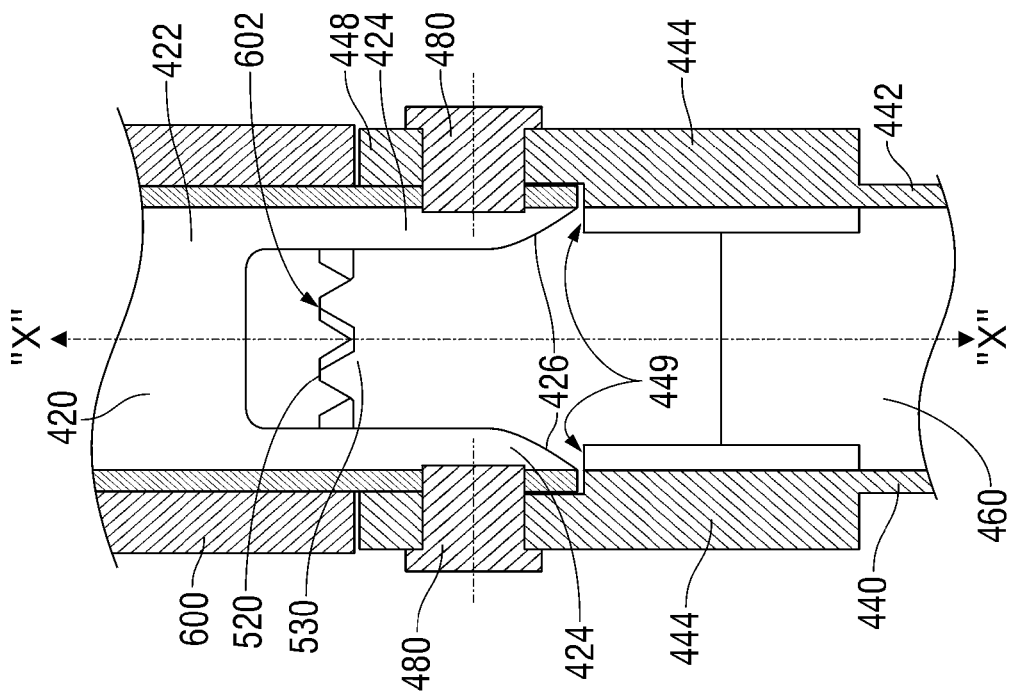
FIG. 8 is a longitudinal cross-section of FIG. 7.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user, while the term "proximal" will refer to that portion of the instrument, apparatus, device or component thereof which is closer to the user. In the following description, well-known functions or constructions are not described in detail to avoid obscuring the present disclosure in unnecessary detail.

Turning now to FIGS. 1-4, one embodiment of a surgical access instrument provided in accordance with the present disclosure is shown generally identified by reference numeral 10. Surgical access instrument 10 defines a longitudinal axis "X-X" and generally includes proximal and distal shaft components 120, 140, respectively, interconnected by an articulation assembly 200, and an outer sleeve 300 disposed about proximal shaft component 120 and translatable relative thereto to articulate distal shaft component 140 relative to proximal shaft component 120 and longitudinal axis "X-X" between a substantially straight, or aligned configuration, wherein both proximal and distal shaft components 120, 140, respectively, are substantially aligned on longitudinal axis "X-X," and an articulated configuration, wherein distal shaft component 140 is articulated off of longitudinal axis "X-X" and relative to proximal shaft component 120. Surgical access instrument 10 further includes a lumen 160 extending longitudinally therethrough that is configured to receive surgical instrumentation (not shown) therethrough for performing a surgical task within an internal surgical site.

Although instrument 10 is shown and described herein as a surgical access instrument 10, it is envisioned that instrument 10 may itself be configured as a shafted surgical instrument for performing a surgical task within an internal surgical site, i.e., instrument 10 may include an end effector assembly (not shown) disposed at the distal end thereof that is selectively articulatable via articulation of distal shaft component 140 relative to longitudinal axis "X-X," to better position the end effector assembly (not shown) for performing the surgical task. Further, instrument 10 may be configured for insertion through a seal anchor member (not shown) positioned within an incision, or opening in tissue to provide sealed access to an internal surgical site. Examples of seal anchor members (not shown) suitable for use in conjunction with instrument 10 are disclosed in U.S. patent application Ser. No. 12/244,024 to Richard et al., filed Oct. 2, 2008, the entire contents of which are hereby incorporated by reference herein.

With continued reference to FIGS. 1-4, proximal and distal shaft components 120, 140, respectively, each define a generally elongated, cylindrical configuration (although other configurations are contemplated) and cooperate with one another to define lumen 160 extending longitudinally therethrough. Proximal shaft component 120 includes a pair of opposed arms 124 extending distally from distal end 122 thereof. Distal shaft component 140 includes a pair of opposed arms 144 extending proximally from proximal end 142 thereof. Arms 124 of proximal shaft component 120 are pivotably coupled to arms 144 of distal shaft component 140 via pivot pins 180, which are engaged to and extend from arms 144 of distal shaft component 140, thus allowing distal shaft component 140 to pivot, or articulate relative to proximal shaft component 120 between the substantially straight configuration (FIG. 1) and the articulated position (FIG. 2). More specifically, as will be described in greater detail below, pivot pins 180 are engaged to (or monolithically formed with) pinion gears 230 of articulation assembly 200 to facilitate articulation of proximal and distal shaft components 120, 140, respectively, relative to one another.

Arms 124, 144 may define complementary-shaped arcuate surfaces 126, 146, respectively, that are configured to mate with one another to facilitate smooth and consistent pivoting of distal shaft component 140 relative to proximal shaft component 120. Surface 126 and/or surface 146 may also include one or more stop features, e.g., stop 148, configured to inhibit articulation of distal shaft component 140 beyond a certain configuration. For example, stop 148 inhibits articulation of distal shaft component 140 beyond the substantially straight configuration such that articulation of distal shaft component 140 is only permitted in one direction. However, it is also envisioned that distal shaft component 140 be articulatable off of longitudinal axis "X-X" in either direction.

As best shown in FIG. 3, arms 124, 144 are disposed towards the outer periphery of shaft components 120, 140, respectively, such that arms 124, 144 do not substantially interfere with lumen 160. Accordingly, surgical instrumentation (not shown) having similar, but slightly smaller diameters, as compared to the diameter of lumen 160 of surgical access instrument 10 may be inserted therethrough for performing a surgical task within an internal surgical site.

Referring again to FIGS. 1-4, outer sleeve 300 is disposed about proximal shaft component 120 and is engaged to articulation assembly 200 at distal end 302 thereof. Outer sleeve 300 further includes a rim 310 disposed at proximal end 304 thereof that is configured to facilitate grasping and manipulation of outer sleeve 300 relative to proximal shaft component 120. As mentioned above, outer sleeve 300 is longitudinally translatable along longitudinal axis "X-X" and relative to proximal shaft component 120 between a proximal position, corresponding to the substantially straight configuration of distal shaft component 140, and a distal position, corresponding to the articulated configuration of distal shaft component 140. Alternatively, rim 310 may be grasped and maintained in a stationary position as proximal shaft component 120 is translated relative thereto to articulate distal shaft component 140 relative to longitudinal axis "X-X."

Articulation assembly 200 includes a pair of opposed brackets 210 engaged to distal end 302 of outer sleeve 300 and extending distally therefrom. Although surgical access instrument 10 is shown including a pair of brackets 210 and corresponding pinion gears 230, it is also envisioned that only one bracket 210 and pinion gear 230 be provided. Each bracket 210 extends along one of arms 124 of proximal shaft component 120 and one of arms 144 of distal shaft component 140 on the outwardly-facing side thereof. As such, brackets 210 do not interfere with lumen 160 extending through surgical access instrument 10. Brackets 210 of articulation assembly 200 each also define an elongated slot 220 therethrough. Slots 220 each define a longitudinally-extending toothed surface, or rack 225 on an interior surface thereof that are each configured to engage a pinion gear 230 therein. Pinion gears 230, as mentioned above, are engaged to, or formed with pivot pins 180, which, in turn, are engaged to arms 144 of distal shaft component 140 and are pivotably coupled to arms 124 of proximal shaft component 120. Due to this configuration, translation of brackets 210 relative to proximal and distal shaft components 120, 140, respectively, urges pinion gears 230 to rotate and translate relative to racks 225 of brackets 210 such that distal shaft component 140 is articulated relative to proximal shaft component 120.

Referring still to FIGS. 1-4, the use and operation of surgical access instrument 10 will be described. Initially, as shown in FIG. 1, with surgical access instrument 10 disposed in the substantially straight configuration, wherein proximal and distal shaft components 120, 140, respectively, are disposed about longitudinal axis "X-X," surgical access instrument 10 is inserted into an internal surgical site, e.g., through an access seal member (not shown) disposed within an incision or opening in tissue. In this initial position, pinion gears 230 are disposed towards the proximal ends 227 of racks 225 of brackets 210 of articulation assembly 200.

With surgical access instrument 10 in position at least partially within an internal surgical site, flexible surgical instrumentation (not shown) may be inserted through lumen 160 of surgical access instrument 10 such that the end effector assembly (not shown) thereof extends distally from distal shaft component 140. As can be appreciated, flexible surgical instrumentation (not shown) is advantageous in that, due to its flexibility, the instrumentation (not shown) is similarly articulated upon articulation of surgical access instrument 10 to better position the end effector assembly (not shown) within the internal surgical site.

Referring now to FIG. 2, in order to articulate surgical access instrument 10 from the initial, substantially straight configuration, to the articulated configuration, outer sleeve 300 is translated proximally relative to proximal and distal shaft components 120, 140, respectively. As outer sleeve 300 is translated proximally, brackets 210 of articulation assembly 200 are similarly translated proximally relative to proximal and distal shaft components 120, 140, respectively, and, thus, relative to pinion gears 230, due to the engagement between outer sleeve 300 and brackets 210. Proximal translation of brackets 210 relative to pinion gears 230, as mentioned above, urges pinion gears 230 to rotate in a first direction and translate distally relative to brackets 210 due to the meshed engagement of pinion gears 230 with racks 225. Rotation of pinion gears 230, in turn, effects similar rotation of pivot pins 180 relative to proximal shaft component 120 such that distal shaft component 140 is articulated off of longitudinal axis "X-X" and relative to proximal shaft component 120 to the articulated configuration. Pinion gears 230 may be translated to the distal ends 229 of racks 225, corresponding to the fully articulated configuration of distal shaft component 140.

As can be appreciated, the teeth of racks 225 and the teeth of pinion gears 230 cooperate with one another to define a plurality of incremental articulated positions of distal shaft component 140. Accordingly, racks 225 and/or pinion gears 230 of articulation assembly 200 may be configured to include relative large, more spaced-apart teeth, or relatively small, closer-together teeth, to define coarser or finer incremental articulation positions. Further, the length of racks 225 define the range of articulation of distal shaft component 140 and, thus, may be configured according to a desired degree of articulation of distal shaft component 140 relative to proximal shaft component 120. For example, relatively longer racks 225 permit further translation of pinion gears 230 therealong and, thus, further rotation of pinion gears 230 to articulate distal shaft component 140 further off of longitudinal axis "X-X," while relative shorter racks 225 permit relatively less rotation of pinion gears 230 and, thus, define a smaller range of articulation of distal shaft component 140.

With distal shaft component 140 in the desired position, the end effector assembly (not shown) of the surgical instrumentation (not shown) inserted through lumen 160 of surgical access instrument 10 may be operated and/or manipulated to perform one or more surgical tasks within the internal surgical site. As can be appreciated, surgical access instrument 10 may also be rotated about longitudinal axis "X-X" to permit 360 degree positioning of the end effector assembly (not shown) of the surgical instrumentation (not shown) extending from distal shaft component 140 relative to longitudinal axis "X-X."

In order to return distal shaft component 140 back to the substantially straight configuration, outer sleeve 300 is translated distally relative to proximal and distal shaft components 120, 140, respectively, such that pinion gears 230 are translated proximally through slots 220 and are rotated in a second, opposite direction due to the engagement of pinion gears 230 with racks 225. As such, rotation of pinion gears 230 in the opposite direction articulates distal shaft component 140 back towards longitudinal axis "X-X" and, ultimately, back to the substantially straight configuration wherein stop 148 inhibit further articulation of distal shaft component 140 beyond the substantially straight configuration. With distal shaft component 140 disposed in the substantially straight configuration, the surgical instrumentation (not shown may be removed from lumen 160 of surgical access instrument 10 and surgical access instrument 10 may be removed from the internal surgical site.

Figure 7:
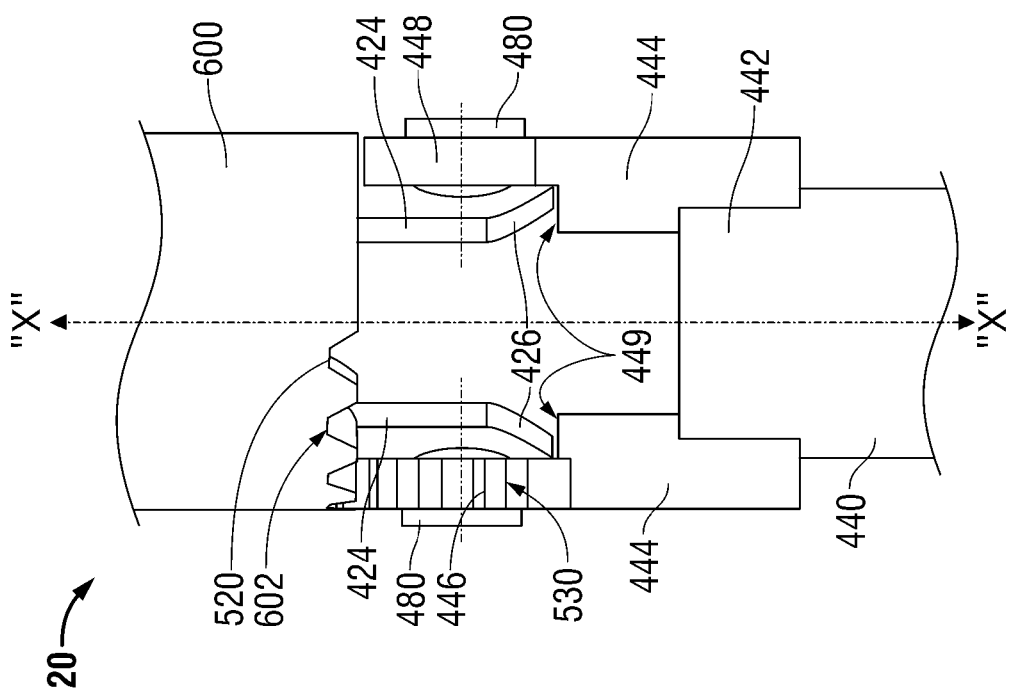
FIG. 7 is a top view of the articulation assembly of the surgical access instrument of FIG. 5.
Figure 10:
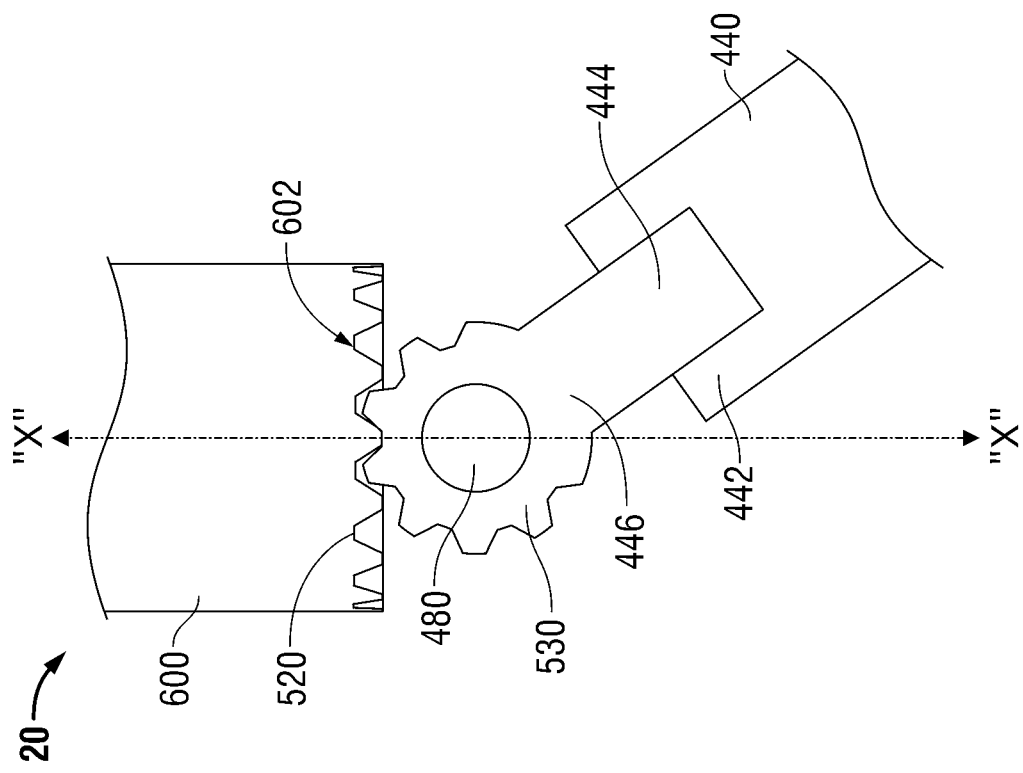
FIG. 10 is a side view of the articulation assembly of the surgical access instrument of FIG. 5, wherein the articulation assembly is disposed in the articulated configuration.
Figure 9:
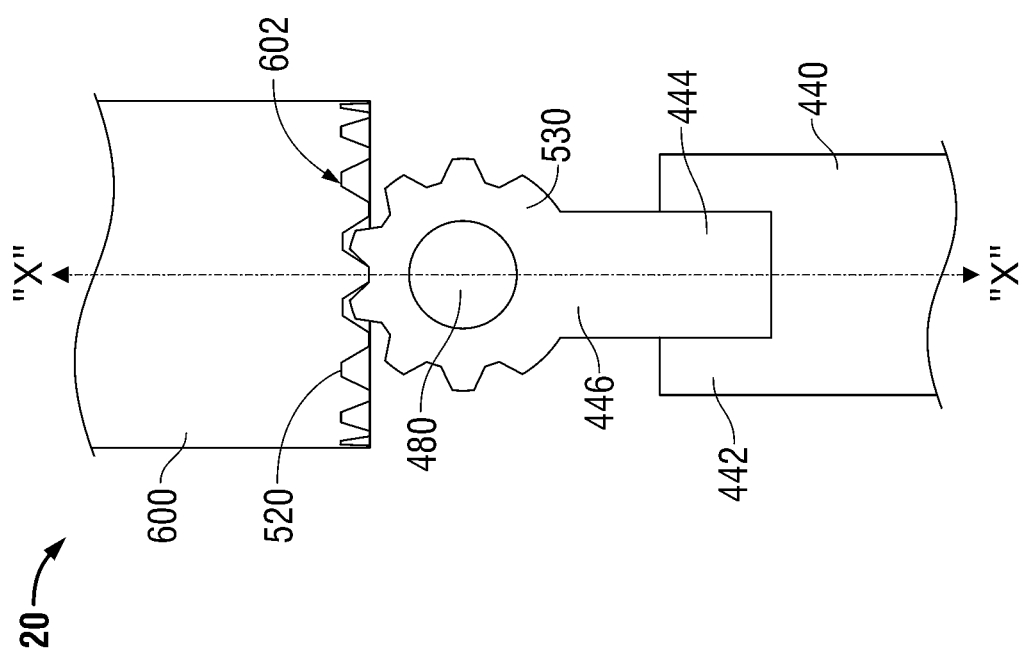
FIG. 9 is a side view of the articulation assembly of the surgical access instrument of FIG. 5, wherein the articulation assembly is disposed in the substantially straight configuration.

Turning now to FIGS. 5-10, another embodiment of a surgical access instrument is shown generally identified by reference numeral 20. Surgical access instrument 20 is similar to surgical access instrument 10 (FIGS. 1-4) in that surgical access instrument 20 includes proximal and distal shaft components 420, 440, respectively, that are articulatable relative to one another between a substantially straight, or aligned configuration (FIG. 9), and an articulated configuration (FIG. 10) to facilitate access to an internal surgical site. Accordingly, any of the features discussed above with respect to surgical access instrument 10 (FIGS. 1-4), to the extent consistent with surgical access instrument 20, may apply similarly to surgical access instrument 20.

With continued reference to FIGS. 5-10, surgical access instrument 20 defines a longitudinal axis "X-X" and includes proximal and distal shaft components 420, 440, respectively, that are interconnected by an articulation assembly 500. An outer sleeve 600 is disposed about proximal shaft component 420 and is rotatable relative thereto and about longitudinal axis "X-X" in order to articulate distal shaft component 440 relative to proximal shaft component 420 between the substantially straight and articulated configurations. Further, proximal and distal shaft components 420, 440, respectively, cooperate to define a lumen 460 extending longitudinally therethrough and configured to permit passage of surgical instrumentation (not shown) therethrough, although instrument 20 may alternatively be configured as an articulatable surgical instrument having an end effector (not shown) disposed at the distal end thereof for performing a surgical task within an internal surgical site.

Proximal and distal shaft components 420, 440, respectively, of surgical access instrument 20 each define a generally elongated, cylindrical configuration (although other configurations are contemplated). Proximal shaft component 420 includes a pair of opposed arms 424 extending distally from distal end 422 thereof, while distal shaft component 440 includes a pair of opposed arms 444 extending proximally from proximal end 442 thereof. A pivot pin 480 is engaged to and extends from each of arms 444 of distal shaft component 440 and is pivotably coupled to one of the arms 424 of proximal shaft component 420. Further, the free end 446 of one of arms 444 of distal shaft component 440 defines a pinion gear 530 disposed about the pivot pin 480 thereof. The other arm 444 may similarly include a pinion gear 530 or, as shown, may define an annular free end 448 disposed about the pivot pin 480 thereof. As can be appreciated, the pivotable engagement between proximal and distal shaft components 420, 440, respectively, permits articulation of distal component 440 relative to proximal component 420 between the substantially straight and articulated configurations, as will be described in greater detail below.

Arms 424 of proximal shaft component 420 may define mating surfaces 426 configured to mate with surfaces 449 of arms 444 of distal shaft component 440 one another to facilitate pivoting of distal shaft component 440 relative to proximal shaft component 420 and/or to inhibit articulation of distal shaft component 440 beyond a certain configuration. For example, surfaces 426 may be configured to inhibit articulation of distal shaft component 440 beyond the substantially straight configuration such that articulation of distal shaft component 440 is only permitted in one direction. However, it is also envisioned that distal shaft component 440 be articulatable off of longitudinal axis "X-X" in either direction.

Continuing with reference to FIGS. 5-10, outer sleeve 600 is disposed about proximal shaft component 420 and includes a rim 610 disposed at proximal end 604 thereof that is configured to facilitate grasping and rotating outer sleeve 600 relative to proximal shaft component 420 (or for maintaining outer sleeve 600 in stationary position as proximal shaft component 420 is rotated relative thereto). Outer sleeve 600 is rotatable about longitudinal axis "X-X" and relative to proximal shaft component 420 between a first position, corresponding to the substantially straight configuration of distal shaft component 440, and a second position, corresponding to the articulated configuration of distal shaft component 440. More specifically, outer sleeve 600 defines an annular rack 520, circumferentially disposed about at least a portion of distal surface 602 of outer sleeve 600, that is configured to engage pinion gear 530 disposed on one of the arms 444 of distal shaft component 440 in meshed engagement therewith such that rotation of outer sleeve 600 about longitudinal axis "X-X" urges pinion gear 530 to rotate to articulate distal shaft component 440 off of longitudinal axis "X-X." The portion of distal surface 602 that does not include annular rack 520 defines a relatively smooth surface and is configured to permit rotation and translation of annular member 448 of the other arm 444 of distal shaft component 440 therealong during articulation of distal shaft component 440.

The use and operation of surgical access instrument 20 is similar to that of surgical access instrument 10 (FIGS. 1-4) and, thus, only the differences will be described hereinbelow to avoid unnecessary repetition.

In order to articulate distal shaft component 440 from the substantially straight position (FIG. 9) to the articulated position (FIG. 10), outer sleeve 600 is rotated about longitudinal axis "X-X" and relative to proximal and distal shaft components 420, 440, respectively. This rotation of outer sleeve 600 urges pinion gear 530 to rotate relative to and translate along annular rack 520 defined on distal surface 602 of outer sleeve 600 due to the meshed engagement between pinion gear 530 and rack 520. Rotation of pinion gear 530, in turn, pivots distal shaft component 440 relative to proximal shaft component 420 from the substantially straight configuration toward the articulation position. As can be appreciated, rotation of outer sleeve 600 in the opposite direction effects rotation and translation of pinion gear 530 in the opposite direction such that distal shaft component 440 is articulated back towards the substantially straight configuration. Similarly as described above with respect to surgical access instrument 10 FIGS. 1-4), the circumferential length of annular rack 520 may be selected to define a desired range of articulation of distal shaft component 440. Further, the size and/or spacing of the teeth of pinion gear 530 and annular rack 520 may be configured to define a desired incremental, or step size of the articulation positions of distal shaft component 440 as distal shaft component 440 is articulated between the substantially straight configuration and the fully articulated configuration.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical instrument, comprising:
    a proximal shaft component defining a longitudinal axis;
    a distal shaft component pivotably coupled to the proximal shaft component and moveable relative to the proximal shaft component between a substantially aligned configuration, wherein the proximal and distal shaft components are disposed about the longitudinal axis, and an articulated configuration, wherein the distal shaft component is articulated off of the longitudinal axis;
    an articulation assembly including a rack and a pinion gear engaged with one another and configured to permit incremental articulation of the distal shaft component relative to the proximal shaft component between the substantially aligned configuration and the articulated configuration;
    first arms extending from each of the proximal and distal shaft components, the first arms pivotably coupled to one another to permit articulation of the distal shaft component between the substantially aligned configuration and the articulated configuration, the first arms defining mating surfaces configured to facilitate articulation of the distal shaft component relative to the proximal shaft component, at least one of the mating surfaces including a stop feature configured to inhibit articulation of the distal shaft component relative to the proximal shaft component beyond a pre-determined position; and an outer sleeve disposed about the proximal shaft component, the outer sleeve manipulatable relative to the proximal shaft component between a first position and a second position for articulating the distal shaft component between the substantially aligned configuration and the articulated configuration.

2. The surgical instrument according to claim 1, wherein the proximal and distal shaft components cooperate with one another to define a lumen extending longitudinally therethrough for receipt of surgical instrumentation therethrough.

3. The surgical instrument according to claim 1, wherein each of the proximal and distal shaft components includes a second arm, the first and second arms of the proximal shaft component pivotably coupled to the respective first and second arms of the distal shaft component to permit articulation of the distal shaft component between the substantially aligned configuration and the articulated configuration.

4. The surgical instrument according to claim 1, wherein the outer sleeve includes a proximal rim disposed at the proximal end thereof, the proximal rim configured to facilitate manipulation of the outer sleeve.

5. The surgical instrument according to claim 1, wherein the outer sleeve is longitudinally translatable along the longitudinal axis and relative to the proximal shaft component between the first position and the second position for articulating the distal shaft component between the substantially aligned configuration and the articulated configuration.

6. The surgical instrument according to claim 1, wherein the outer sleeve is rotatable about the longitudinal axis and relative to the proximal shaft component between the first position and the second position for articulating the distal shaft component between the substantially aligned configuration and the articulated configuration.

7. The surgical instrument according to claim 1, wherein the first arms extend from each of the proximal and distal shaft components towards the other of the proximal and distal shaft components.

* * * * *